United States Patent
Kounga et al.

(10) Patent No.: US 9,700,391 B2
(45) Date of Patent: Jul. 11, 2017

(54) METHOD OF MANUFACTURING A PROSTHETIC ELEMENT

(71) Applicant: Straumann Holding AG, Basel (CH)

(72) Inventors: Alain Kounga, Basel (CH); Christoph Appert, Basel (CH); Iwona Dziadowiec, Cracow (PL)

(73) Assignee: STRAUMANN HOLDING AG, Basel (CH)

( * ) Notice: Subject to any disclaimer, the term of this patent is extended or adjusted under 35 U.S.C. 154(b) by 98 days.

(21) Appl. No.: 14/372,605

(22) PCT Filed: Jan. 21, 2013

(86) PCT No.: PCT/EP2013/000168
§ 371 (c)(1),
(2) Date: Jul. 16, 2014

(87) PCT Pub. No.: WO2013/107653
PCT Pub. Date: Jul. 25, 2013

(65) Prior Publication Data
US 2014/0370464 A1    Dec. 18, 2014

(30) Foreign Application Priority Data

Jan. 20, 2012 (EP) .................................... 12000361
Jan. 23, 2012 (EP) .................................... 12000717

(51) Int. Cl.
*A61C 13/00* (2006.01)
*A61K 6/027* (2006.01)
(Continued)

(52) U.S. Cl.
CPC .......... *A61C 13/0018* (2013.01); *A61C 13/00* (2013.01); *A61C 13/0004* (2013.01);
(Continued)

(58) Field of Classification Search
CPC ... C03B 23/047; C03B 32/00; C03B 2205/20; C03B 2205/55; C03B 2205/56;
(Continued)

(56) References Cited

U.S. PATENT DOCUMENTS 2,971,853 A * 2/1961 Stookey .................... C03C 4/02
257/701
3,464,807 A * 9/1969 Pressau ................. C03B 27/012
501/4
(Continued)

FOREIGN PATENT DOCUMENTS

DE    10 2007 011337 A1    9/2008
EP       0 924 171 A1        6/1999
(Continued)

OTHER PUBLICATIONS

International Search Report dated Jul. 31, 2013 in corresponding International Patent Application No. PCT/EP2013/000168.
(Continued)

*Primary Examiner* — Jodi C Franklin
(74) *Attorney, Agent, or Firm* — Oliff PLC (57) ABSTRACT

A process for preparing a prosthetic element comprising a glass-ceramic body. including the steps of
a) providing a basic body comprising an amorphous glass phase and containing the components of the glass-ceramic body to be prepared, and
b) transferring energy to the basic body to induce conversion of a starting phase of the material of the basic body into at least one crystalline phase in a confined region. According to the invention, energy is transferred to the confined region of the basic body by laser irradiating said region with a laser beam having a wavelength of at least 500 nm.

25 Claims, 5 Drawing Sheets

(51) Int. Cl.
    *C03C 10/00*     (2006.01)
    *C03C 23/00*     (2006.01)
    *A61C 13/083*    (2006.01)
    *C03B 32/02*     (2006.01)

(52) U.S. Cl.
    CPC ........ *A61C 13/0022* (2013.01); *A61C 13/083* (2013.01); *A61K 6/0273* (2013.01); *C03C 10/0027* (2013.01); *C03C 23/0025* (2013.01); *C03B 32/02* (2013.01)

(58) Field of Classification Search
    CPC . C03B 33/0222; C03B 33/0235; C03B 33/07; C03B 37/02718; C03B 37/02727; C03B 37/029; C03B 23/006; C03B 23/02; C03B 32/02; C03C 23/0025; C03C 10/00; C03C 25/6233; C03C 2218/345; C03C 23/0005
    USPC .................................. 65/33.1–33.4
    See application file for complete search history.

(56) References Cited

U.S. PATENT DOCUMENTS

| | | | | |
|---|---|---|---|---|
| 6,284,340 | B1* | 9/2001 | Abe .................... | C03C 10/0027 428/141 |
| 6,455,451 | B1* | 9/2002 | Brodkin ................ | A61K 6/033 106/35 |
| 6,514,890 | B1* | 2/2003 | Nagata .................... | C03C 3/097 428/846.9 |
| 6,534,207 | B2* | 3/2003 | Kubota ................... | C03C 10/00 428/697 |
| 7,871,948 | B2* | 1/2011 | Apel ...................... | C03B 32/02 106/35 |
| 2004/0003627 | A1* | 1/2004 | Hashima ................... | C03C 4/12 65/33.2 |
| 2004/0152034 | A1* | 8/2004 | Cummings .......... | A61K 6/0276 433/8 |
| 2007/0042889 | A1* | 2/2007 | Apel ...................... | C03B 32/02 501/5 |
| 2008/0120994 | A1* | 5/2008 | Schweiger .......... | C03C 10/0027 65/33.4 |
| 2008/0230397 | A1* | 9/2008 | Fecher .................... | A61K 6/043 205/674 |
| 2008/0315123 | A1* | 12/2008 | Komatsu ................. | C03C 3/078 250/492.1 |
| 2010/0143868 | A1* | 6/2010 | Hintersehr ......... | A61C 13/0018 433/172 |
| 2010/0303722 | A1* | 12/2010 | Jin .......................... | A61L 27/30 424/9.1 |
| 2010/0310786 | A1* | 12/2010 | Dunne .............. | A61C 13/0004 427/487 |
| 2011/0020423 | A1 | 1/2011 | Elenko | |
| 2011/0030423 | A1* | 2/2011 | Johannes ................ | C03C 3/085 65/21.5 |
| 2011/0081627 | A1* | 4/2011 | Sun .................... | A61C 13/0003 433/199.1 |
| 2012/0237745 | A1* | 9/2012 | Dierkes ................ | A61K 6/0215 428/215 |
| 2013/0149433 | A1* | 6/2013 | Ehrt ..................... | A61K 6/0017 427/2.29 |

FOREIGN PATENT DOCUMENTS

EP  0924171 A1  6/1999
WO  2012/143137 A1  10/2012

OTHER PUBLICATIONS

International Preliminary Report on Patentability mailed Jul. 31, 2014 in International Patent Application No. PCT/EP2013/000168, including ISR and Written Opinion.

* cited by examiner

METHOD OF MANUFACTURING A PROSTHETIC ELEMENT

FIELD OF THE INVENTION

The present invention relates to a process for preparing a prosthetic element comprising a glass-ceramic body, to a prosthetic element obtainable by this process, as well as to the use of said prosthetic element for a dental restoration.

BACKGROUND

Glass-ceramic materials comprise an amorphous (glass) phase and one or more crystalline (ceramic) phases embedded in the amorphous phase. Due to the presence of both an amorphous and a crystalline phase, glass-ceramics share many properties with both glasses and ceramics. They are used in a variety of different technical fields, for example as cooktops, cookware and bakeware, as a substrate for magnetic disks, as high performance reflectors for digital projectors or as prosthetic elements.

Glass-ceramics are of particular interest in the field of restorative dentistry, since there is a high demand for prosthetic elements which exhibit excellent characteristics comparable to those of natural teeth in terms of functionality and appearance.

Prosthetic elements for use in dental restorations, such as crowns, bridges, abutments, onlays and inlays, are today increasingly manufactured by computer aided design/computer aided machining (CAD/CAM) technologies. The fabrication process comprises two decisive stages: a computer-aided design of the restoration and its computer-aided milling. In the stage of milling, the restoration is machined out of a dental material block.

In view of the preparation of a prosthetic element by a CAD/CAM method, it is essential that the material on which the element is based not only has appealing optical properties as well as a high strength and chemical durability. The material should also allow to be machined into the desired shape in an easy manner without undue wear of the tools.

A process for preparing a shaped glass-ceramic dental product comprising the step of machining a respective blank is e.g. proposed in DE-A-19750794. More particularly, DE-A-19750794 relates to a lithium disilicate glass-ceramic and is aiming at a high chemical stability, a high translucency and good mechanical properties of the product. Due to the high strength and toughness imparted by the lithium disilicate crystalline phase, however, it has been shown that application of this method results in increased tool wear during finishing and insufficient edge strength of the restorations prepared especially when their thickness falls within a range of only a few hundreds of micrometers.

U.S. Pat. No. 7,452,836 relates to a process for providing a glass-ceramic which has metastable lithium metasilicate ($Li_2SiO_3$) as main crystalline phase. This lithium metasilicate glass-ceramic has mechanical properties allowing it to be easily machined into the shape of even complicated dental restorations without undue wear of tools. It can be converted by further heat treatment into a lithium disilicate glass-ceramic with very good mechanical properties and translucency.

Although U.S. Pat. No. 7,452,836 allows for achieving materials having a flexural strength which might be sufficient for the restoration of multiple missing teeth in the front (3-unit bridges), its strength is still not sufficient for posterior bridges or large restorations.

A further shortcoming of the method according to U.S. Pat. No. 7,452,836 lies in the fact that crystals are grown throughout the whole volume without any spatial order leading to a homogenous material constitution. This is in contrast to a natural tooth and has important implications regarding both aesthetic and mechanical properties of the dental restoration, as shown in the following:

Natural teeth consist of a hard, inert and acellular enamel supported by the less mineralized, more resilient and vital hard tissue dentin. Because of its exceptionally high mineral content, enamel is a brittle tissue unable to withstand the forces of mastication without fracture unless it has the support of the more resilient dentin.

Enamel and dentin do not only differ in their mechanical and thermal properties, namely their compressive strength, elastic modulus and coefficient of thermal expansion, but also in their appearance. Whereas enamel is translucent and varies in colour from light yellow to grey-white, dentin is yellow. In a natural tooth, the thickness of enamel varies from a maximum of approximately 2.5 mm to a fraction thereof. This variation influences the tooth's appearance because the underlying dentin is seen through the thinner enamel region, whereas it gradually fades out towards thicker ones.

In summary, a natural tooth has thus an inhomogeneous structure different than in the glass-ceramic of U.S. Pat. No. 7,452,836 and can thus both with regard to aesthetic appearance and mechanical stability not be mimicked perfectly by the material disclosed in U.S. Pat. No. 7,452,836.

Aiming at a material mimicking the colour gradients in a natural tooth, WO 2010/010082 discloses a form-stabilized material comprising a first component and a second component, the second component having a different pigmentation than the first component and being disposed in the first component such that the boundary surface between the components represents a spatially curved surface. However, as a feldspathic ceramic, the material according to WO 2010/010082 does not exhibit suitable mechanical properties for indications such as multiple anterior or posterior unit-bridges.

Further, a method for manufacturing structured prostheses from a blank comprising at least one layer of high abrasive resistance, at least one layer of high flexural strength and at least one layer of lower hardness and strength is disclosed in U.S. Pat. No. 5,939,211. During the milling of the restoration, material removal is performed in such a manner that layers with high strength constitute a reinforcing structure.

In both the materials according to U.S. Pat. No. 5,939,211 and WO 2010/010082, the presence of physically distinct component layers and thus of an interface between different components has as a rule a negative impact on the overall stability of the dental restoration. Also, the methods according to these publications are relatively laborious.

Considering the drawbacks of the state of the art, it would be highly desirable to provide a process for the preparation of a prosthetic element comprising a glass-ceramic body, which allows precise adjusting of the properties to the actual need in a simple and effective manner.

SUMMARY OF THE INVENTION

In particular for achieving dental restorations, with both high aesthetics and superior mechanical properties, preparation of a prosthetic element comprising a glass-ceramic body would be desirable for which different mechanical and optical properties can be adjusted precisely in different regions of one and the same body without any limitations concerning the position of the region within the body.

The object of the present invention is thus to provide a simple and effective process for preparing a prosthetic element comprising a glass-ceramic body, the properties of which can be adjusted in a very precise manner.

Particularly, the process shall allow the type and proportion of the crystalline phase to be precisely adjusted in a confined region within the body without being locally limited to specific areas of the body, thus allowing mimicking the structure of the natural counterpart—e.g. a tooth.

More particularly, the process shall allow preparing a prosthetic element comprising regions of different crystalline phases. It shall further allow preparing a prosthetic element comprising regions of different crystalline phases changing from one region to another in a gradual manner.

According to a first aspect, the present invention relates to a process for preparing a prosthetic element comprising a glass-ceramic body, said process comprising the steps of
a) providing a basic body comprising an amorphous glass phase and containing the components of the glass-ceramic body to be prepared, and
b) transferring energy to the basic body.

By the transfer of energy, conversion of a starting phase of the material of the basic body into at least one crystalline phase is induced in a confined region.

According to the present invention, energy is transferred to the confined region of the basic body by laser irradiating said region with a laser beam having a wavelength of at least 500 nm.

Due to the use of a laser beam, the present invention allows energy to be transferred to the basic body in a focused manner. It has been found that by using a laser having a wavelength as specified above, a conversion of a starting phase into the at least one crystalline phase can be effectively induced in the laser irradiated region. In other words, phase conversion can be induced precisely in a confined region of the basic body without affecting other regions in which the conversion shall not take place. Ultimately, this allows for achieving a prosthetic element comprising a glass-ceramic body having a structure mimicking the structure of a natural tooth.

The term "confined region" is to be interpreted broadly and encompasses any region confined by respective virtual boundaries, said boundaries separating the material of the confined region from the remaining material of the basic body or the glass-ceramic body, respectively. Typically, the term "confined region" is to be understood as a three-dimensional region, the volume of which being smaller than the volume of the basic body or the glass-ceramic body, respectively.

Thus, the material of the confined region is at least partially surrounded by the remaining material of the basic or the glass-ceramic body not being converted according to the present invention or being converted in a manner different than the confined region.

The process encompasses both embodiments in which the starting phase is an amorphous phase as well as embodiments in which the starting phase is a crystalline phase different from the crystalline phase to be obtained by the conversion.

According to a preferred embodiment, the starting phase is amorphous. More preferably, the basic body is made of an at least approximately thoroughly amorphous glass material, i.e. a glass material without any crystallites embedded in the glass matrix.

If the conversion step relates to the conversion of an amorphous phase into a crystalline phase, the process typically comprises a nucleation step prior to the crystallization steps.

Without wanting to be bound by the theory, it is assumed that the conversion of a starting phase into the at least one crystalline phase is a result of the heating of the basic body in the laser irradiated region caused by the absorption of energy. According to a preferred embodiment, the basic body is thus heated in the region through laser irradiation. If the basic body lies on a substrate during laser irradiation, it is assumed that part of the laser light is transmitted and fully reflected by the underlying substrate. This reflected light may lead to additional heating of the material, which further promotes crystallization. However, it is also thinkable that conversion is at least partly induced by the light energy of the laser beam which leads to excitation of atoms and molecules in the glass matrix of the basic body.

It has been found that a particularly effective crystallisation can be achieved by using a laser beam having a wavelength of at least 600 nm, more preferably at least 700 nm, most preferably at least 800 nm.

In order to accelerate the conversion process, two or more laser beams can be collimated to increase the effective energy absorbed by the basic body.

It is also thinkable that laser irradiation is performed by superposed application of two or more laser beams. This way, energy can be bundled precisely in the intersection point of the two or more laser beams.

In this regard it is emphasized that the process of the present invention is not confined to the local surface area of the body, but allows selective and controlled formation of a crystalline phase in a specific region throughout the basic body and in particular in the interior of the body remote from the surface. This is in contrast to e.g. US 2008/0213727 which is directed to the formation of a gradient in the surface area of a body.

As will be discussed below, the process may also comprise pre-heating of the basic body in addition to laser irradiation. Typically, the basic body is thereby preheated to a first temperature before laser irradiation. Thereby, the heating time and the risk of formation of undesired stress inside the glass matrix can be reduced.

Preferably, the first temperature mentioned above, i.e. the (pre-)heating temperature, lies in a range from about 300° C. to about 750° C., more preferably from about 400° C. to about 750° C., even more preferably from about 600° C. to about 750° C., and most preferably is at about 660° C.

Heating of the basic body may e.g. be performed by placing it into a heated environment, such as a heating furnace. Alternatively or additionally, the basic body may be placed on a heated supporting plate.

If the temperature distribution in the surrounding space is non-uniform, as it is e.g. the case when the basic body is placed on a heated supporting plate, a temperature gradient can be established in the basic body. By laser irradiating the basic body with the temperature gradient established therein, a very selective crystallisation can be achieved in the interior of the basic body, more particularly in the region where the temperature required for crystallisation is achieved.

Depending on the composition of the basic body, more or less laser energy may be absorbed by the material of the basic body. In order to safeguard that the absorbed laser energy suffices to induce crystallization, the basic body and, consequently, the glass-ceramic body comprises at least one ion which is able to increase the absorption of laser energy (in the following referred to as "absorption-increasing ion").

For example, the glass-ceramic body comprises an absorption-increasing ion selected from the group consisting of $Nd^{3+}$, $Fe^{2+}$, $Fe^{3+}$, $V^{2+}$, $V^{3+}$, $V^{4+}$, $V^{5+}$, $Co^{2+}$, $Cr^{4+}$, $Cr^{6+}$ and $Mn^{2+}$, and mixtures thereof. By the presence of an absorption-increasing ion, the material's absorption of laser energy is increased allowing for a phase conversion even in the case that the laser irradiation period is relatively short.

It has been found that a continuous wave (cw) laser, and more particularly a continuous wave (cw) high power diode laser, is particularly suited for the process of the present invention since continuous irradiation of the sample enables a slow heating that promotes crystal growth and helps avoid thermal shock as well as stress inside the glass matrix.

In particular, the use of a continuous wave (cw) laser allows gentle heating of a confined region within the basic body with eventual local relaxation, thus allowing to avoid local melting or sublimation that might lead to strain incompatibilities and consequently to the formation of cracks within the body. This is in contrast to e.g. a pulsed laser, specifically a pulsed laser the beam of which having a wavelength lower than 500 nm, as will be shown by way of the Comparative Examples below.

It has further been found that a laser having a fluence in the range of 600 $W/cm^2$ to 700 $W/cm^2$ is particularly suitable for the process of the present invention.

Other lasers such as a femtosecond laser, a picosecond laser, a nanosecond laser, a $CO_2$-Laser or a Nd:YAG laser are also thinkable.

If the process of the present invention is used in the context of manufacturing of the prosthesis in a CAD/CAM process, laser irradiation for inducing phase conversion can be performed before or after machining of the material block.

As mentioned, the present invention also relates to the use of the prosthetic element comprising the glass-ceramic body for a dental restoration.

In view of its use for dental restorations, the glass-ceramic body preferably comprises as the two main crystalline phases a lithium disilicate phase and a lithium aluminosilicate phase, as will be shown below.

This glass-ceramic body can be obtained by using a composition comprising 65 to 72 wt-% $SiO_2$, at least 8 wt-% $Li_2O$ and at least 8 wt-% $Al_2O_2$ based on the total weight of the composition.

Respective glass compositions have been shown to allow for the formation of a great variety of different crystalline phases by the process of the present invention.

According to a particularly preferred embodiment, the composition comprises at least 10.1 wt-% of $Li_2O$. It is further preferred that it comprises at least 10.1 wt-% of $Al_2O_3$.

Preferably, the composition comprises at most 15 wt-% of $Li_2O$ and/or at most 15 wt-% of $Al_2O_2$.

According to a particularly preferred embodiment, the proportion of $Li_2O$ to $Al_2O_2$ is at least 1:1, preferably about 3:2.

In general, the composition further comprises 0 to 2 wt-% $K_2O$, 1 to 4 wt-% $Na_2O$ and 0 to 1.5 wt-% $CeO_2$.

Depending on the final glass-ceramic body to be achieved, different crystallization agents can be used in the glass composition. Typically, the composition comprises 0 to 1.5 wt-% CaO, 0 to 1.0 wt-% MgO, 0 to 1.5 wt-% $B_2O_3$, 1 to 5 wt-% $P_2O_5$, 0 to 3 wt-% $CaF_2$, 0 to 2.0 wt-% $AlF_3$, 0 to 1.0 wt-% Ag, 0 to 5 wt-% $ZrO_2$ and 0 to 4 wt-% $TiO_2$ based on the total weight of the composition. A glass composition being devoid of $ZrO_2$ and $TiO_2$ is particularly preferred for achieving a relatively high content of a lithium disilicate crystalline phase.

Exemplary embodiments of the glass composition of the basic body are given in Table 1:

TABLE 1

| Component | Composition 1 (wt-%) | Composition 2 (wt-%) | Composition 3 (wt-%) | Composition 4 (wt-%) |
|---|---|---|---|---|
| $SiO_2$ | 68 | 69.5 | 66.5 | 66.5 |
| $Li_2O$ | 10.5 | 10.5 | 12 | 10.5 |
| $Al_2O_3$ | 10.5 | 10.5 | 12 | 10.5 |
| $K_2O$ | 0.5 | 0.5 | 0.4 | 0.45 |
| $Na_2O$ | 2.5 | 1.0 | 1.05 | 4.0 |
| $ZrO_2$ | 0.5 | 0.5 | 3.0 | 0.5 |
| $CeO_2$ | 1.4 | 1.5 | 1.5 | 1.4 |
| $V_2O_5$ | 0.05 | 0.05 | 0.05 | 0.05 |
| CaO | 1.55 | 1.45 | 0 | 0 |
| $P_2O_5$ | 4.5 | 4.5 | 3.4 | 4.5 |

By the process of the present invention and in particular by using a composition as defined above in the process of the present invention (see Example 1 and FIGS. 1-5), a glass-ceramic body having a very high flexural strength can be achieved, in particular a glass-ceramic body having a flexural strength higher than 400 MPa, preferably higher than 450 MPa, and more preferably higher than 500 MPa, as determined by the three-point flexure test according to ISO 6872. This body has, thus, a flexural strength sufficient to be used as a fully anatomic prosthetic element.

In order to achieve a prosthetic element very closely mimicking a natural tooth, it is particularly preferred that a first region (17 in FIGS. 3-5) of the basic body 11 be subjected to a first conversion step to induce formation of a crystalline phase A in the first region and a second region 18 of the basic body 11 different from the first region be subjected to a second conversion step to induce formation of a crystalline phase B in the second region.

It is thereby particularly preferred that the crystalline phase A formed in the first region is different from the crystalline phase B formed in the second region.

It is further preferred that the proportion of the crystalline phase A is higher in the first region than in the second region and the proportion of the crystalline phase B is higher in the second region than in the first region. The term "proportion" of the respective crystalline phase is in the context of the present invention to be understood as volume-% based on the total volume of the final prosthetic element.

As mentioned, the process of the present invention allows the type and proportion of crystalline phases A and B to be adjusted in a very simple and precise manner, e.g. by correspondingly setting the rate of energy transferred and the duration of irradiation by the laser beam(s). Ultimately, this allows the inhomogeneous structure of e.g. a natural tooth to be accurately mimicked.

As for the conversion steps, embodiments are encompassed in which the first region is exclusively subjected to the first conversion step and the second region is exclusively subjected to the second conversion step. In particular if the second conversion step is at a higher temperature range, it is also thinkable that the second region is also subjected to the first conversion step before it is subjected to the second conversion step. In this regard, it is to be noted that the second region may either be a subregion of the first region or spatially separated from the first region.

Optionally, as mentioned above, laser irradiation may also be performed by superposed application of two or more laser beams. Also, by the subsequent application of two or more laser beams with different energy, several conversion steps can be effected in sequence.

As the range of the crystallization temperature for obtaining the desired crystalline phase is relatively narrow, the basic body can be (pre-)heated beyond 500° C. without inducing substantial crystallization of lithium disilicate or lithium aluminosilicate. Given the composition's further characteristic that the thermal conductivity of the crystalline phase(s) is more or less similar, a homogenous heat distribution throughout the body can be obtained; thus, heat concentration in the irradiated region can be minimized, allowing for a relaxation of the material of the body. This relaxation is increased as the temperature of the treated body slowly decreases to pass the glass transition temperature and finally to cool down to room temperature. A typical cooling rate is between 1K/min and 10K/min.

In view of the formation of two crystalline phases A and B in the $SiO_2$—$Li_2O$—$Al_2O_3$ material mentioned above, the basic body is typically heated to a temperature in the range from 530° C. to 570° C. for the nucleation step, followed by at least two crystallization steps selected from the ranges from 620° C. to 680° C., from 800° C. to 820° C. and from 825° C. to 830° C., depending on the desired crystalline phases to be formed and their proportions in relation to each other and to the amorphous phase. Thus at the most preferred (pre-)heating temperature of about 660° C., besides nucleation, crystallisation of $Li_2SiO_3$ and of traces of lithium aluminosilicate will occur and, depending on the starting material, also $Li_3PO_4$. The duration for any of these steps typically vary in the range from seconds to about 3 hours, preferably seconds to minutes, also depending on the desired crystalline phases to be formed and their proportions the range may be from minutes to about 3 hours or minutes to about 1 hour. Again, a typical cooling rate is between 1K/min and 10K/min.

By appropriately setting the laser irradiation parameters for achieving the required temperature ranges, a glass-ceramic material comprising different crystalline phases, such as lithium disilicate, lithium metasilicate, lithium phosphate, lithium aluminosilicate, and cristobalite, can thus be achieved. Also, the respective proportions of the crystalline phases can be adjusted to the actual needs.

It is in this regard particularly preferred that the at least one crystalline phase, and more particularly crystalline phase A and/or crystalline phase B, comprises at least one component selected from the group consisting of lithium metasilicate ($Li_2SiO_3$), lithium disilicate ($Li_2Si_2O_5$), a lithium aluminosilicate ($LiAlSi_2O_6$, $LiAlSiO_4$, $LiAlSi_3O_8$, $LiAlSi_4O_{10}$) and/or $Li_3PO_4$. This allows an almost unlimited adjustment of properties of the prosthetic element by suitably choosing the crystalline phases and the proportion in which they are present. A particularly preferred combination is thereby $LiAlSi_2O_6$, $LiAlSi_3O_8$ and $Li_2Si_2O_5$ further comprising $Li_3PO_4$.

According to a preferred embodiment, the glass-ceramic body is at least approximately devoid of $Li_2(TiO)SiO_4$ and/or $SiO_2$, specifically quartz, cristobalite and tridymite.

According to a further preferred embodiment, the prosthetic element comprises a glass-ceramic body comprising lithium aluminosilicate as main crystalline phase. This is in contrast to a glass-ceramic body comprising lithium disilicate ($Li_2Si_2O_5$) as main crystalline phase.

If two different crystalline phases A and B are to be prepared in view of a prosthetic element for a dental restoration, it is particularly preferred that the crystalline phase A comprises lithium disilicate as main crystalline phase and crystalline phase B comprises lithium aluminosilicate as main crystalline phase.

Regarding the co-existence of a lithium disilicate phase and a lithium aluminosilicate phase, desirable new properties can be achieved. In particular, a glass-ceramic body can be achieved having mechanical properties between the properties of lithium aluminosilicate glass-ceramics having excellent thermal properties and relatively moderate mechanical properties (with a flexural strength of 75 to 150 MPa and a fracture toughness $K_{1c}$ of 1 to 2 MPa·m$^{1/2}$) and of lithium disilicate glass-ceramic having a high strength (with a flexural strength of 350 to 400 MPa and a fracture toughness $K_{1c}$ of 2.3 to 2.9 MPa·m$^{1/2}$) and relatively low thermal properties (with a coefficient of thermal expansion of 80 to 120·10$^{-7}$ deg$^{-1}$).

According to a preferred embodiment of the present invention, a first crystalline phase of $Li_2Si_2O_5$ (lithium disilicate) is converted into a further crystalline phase selected from the group consisting of $LiAlSi_2O_6$, $LiAlSiO_4$, $LiAlSi_3O_8$ and $LiAlSi_4O_{10}$. The second crystalline phase is thus a lithium aluminosilicate; among the group mentioned, $LiAlSi_2O_6$ and $LiAlSi_3O_8$ are preferred. In the context of the present invention the term "lithium aluminosilicate" stands for either one or a combination of the above compounds.

According to a particularly preferred embodiment Example 1 and FIGS. 3-6), the prosthetic element 19 has an enamel area and a dentin area corresponding to the respective areas of a natural tooth, with the first region 17 (containing lithium disilicate as main crystalline phase) being arranged in the enamel area and the second region 18 (containing lithium aluminosilicate as main crystalline phase) being arranged in the dentin area.

This is of particular relevance from an aesthetical point of view, since regions comprising a lithium disilicate crystalline phase generally are translucent resembling enamel whereas regions comprising a lithium aluminosilicate crystalline phase are opaque resembling dentin.

By performing the process of the present invention, a prosthetic element comprising a glass-ceramic body can thus be obtained comprising inhomogenously distributed crystalline phases imparting an inhomogenous colour distribution resembling the colour distribution of a natural tooth.

Also with regard to the mechanical properties, the structure of a natural tooth can be accurately mimicked by the inhomogenously distributed crystalline phases, as the lithium disilicate phase imparts a higher strength than the lithium aluminosilicate phase corresponding to the natural situation with the enamel having a higher strength than the dentin.

In addition, the high chemical resistance of the lithium disilicate glass-ceramic region attributes to its feasibility for an enamel-like region.

Furthermore, due to the lithium aluminosilicate being opaque, a metal abutment or implant can be shielded from shining through the restoration by suitably arranging the lithium aluminosilicate phase within the glass-ceramic body.

Notwithstanding that the present invention allows the precise formation of different crystalline phases in spatially separated regions, it also allows different crystalline phases to be achieved changing from one region to another in a gradual manner. This is of particular relevance concerning the use of the prosthetic element for a dental restoration, since also in a natural tooth the different structural components change in a gradual manner.

The process of the present invention is therefore preferably carried out in a manner such that the proportion of crystalline phase A (in a first region) changes to crystalline phase B (in a second region) in a gradual manner.

As mentioned, it is in this regard thinkable that the basic body is first heated to a first temperature in a heated environment before laser irradiation performed. If applicable, a temperature gradient can be achieved in the basic body by appropriately placing the body in a heated reaction chamber, i.e. a heating furnace, in which such a temperature gradient is present, thus leading to a gradual change of the crystalline phase composition along the gradient. Alternatively or additionally, a heated supporting plate may be used.

Thus, different crystalline phases changing from one region to another in a gradual manner can be formed. This has not only important implications in view of the aesthetic appearance of the prosthetic element but also in view of its mechanical stability.

Regarding e.g. the coefficient of thermal expansion, which is different in a lithium disilicate glass-ceramic region than in a lithium aluminosilicate glass-ceramic region, a smooth transition can thus be achieved. That way, any stability problems which might arise at an interface of different materials/crystal structures can be avoided and a favourable stress distribution is obtained.

This is of also particular interest in view of the CAD/CAM machining of the prosthetic element comprising the glass-ceramic body since adjustment of the formation of different crystalline phases in different regions of the body further allows a favourable distribution of stresses which strengthens the body and makes it less prone to fracture.

If machining is carried out after conversion into the final crystalline phase(s), the distribution of the crystalline phase(s) can be adjusted such that the areas to be machined off the block are preferably predominantly of a softer material than e.g. the areas which will be present in the ultimate restoration.

As mentioned above, the present invention allows for adapting physical subtleties and colour nuances in one single body by a focused phase conversion. Laser irradiation can, however, also be used for providing a gloss to the prosthetic element. Thereby, the outermost surface 20 (See FIG. 5) of the basic body 19A or the glass-ceramic body is melted by means of laser irradiation followed by solidification of the melted material. This further contributes to the aesthetical appearance of the prosthetic element.

With regard to the CAD/CAM method, laser irradiation can further be used for cutting the basic body or the glass-ceramic body into the desired shape for the final prosthetic element. Thereby, the machining step of a conventional CAD/CAM method and, consequently, the use of expensive diamond-cutting tools that have limited service life due to wear can be avoided. Ultimately, a fully automated and fully controlled production process for ready-to-insert dental prosthesis can be achieved using only laser equipment with regard to the cutting of the material block and the formation of crystalline phase(s) within the material.

If cutting of the block is to be carried out using laser irradiation, a short pulse laser is preferably used.

According to a further aspect, the present invention also relates to a prosthetic element obtainable by the process described above. As mentioned, the prosthetic element is preferably a prosthetic element for a dental restoration, which encompasses both single-unit restorations as well as multi-unit bridges. The prosthetic element of the present invention can essentially consist of the glass-ceramic body or may comprise further components.

DETAILED DESCRIPTION

The present invention is further illustrated by way of the following examples.

EXAMPLES

Glass Composition of Basic Body

A glass composition comprising 68 wt-% $SiO_2$, 10.5 wt-% $Li_2O$, 10.5 wt-% wt-% $Al_2O_3$, 0.5 wt-% $K_2O$, 2.5 wt-% $Na_2O$, 4.5 wt-% $P_2O_5$, 0.5 wt-% $ZrO_2$, 1.45 wt-% CaO, 1.5 wt % $CeO_2$, 0.05 wt % $V_2O_5$ is provided according to a standard procedure known to the skilled person.

Example 1

Figure 1:
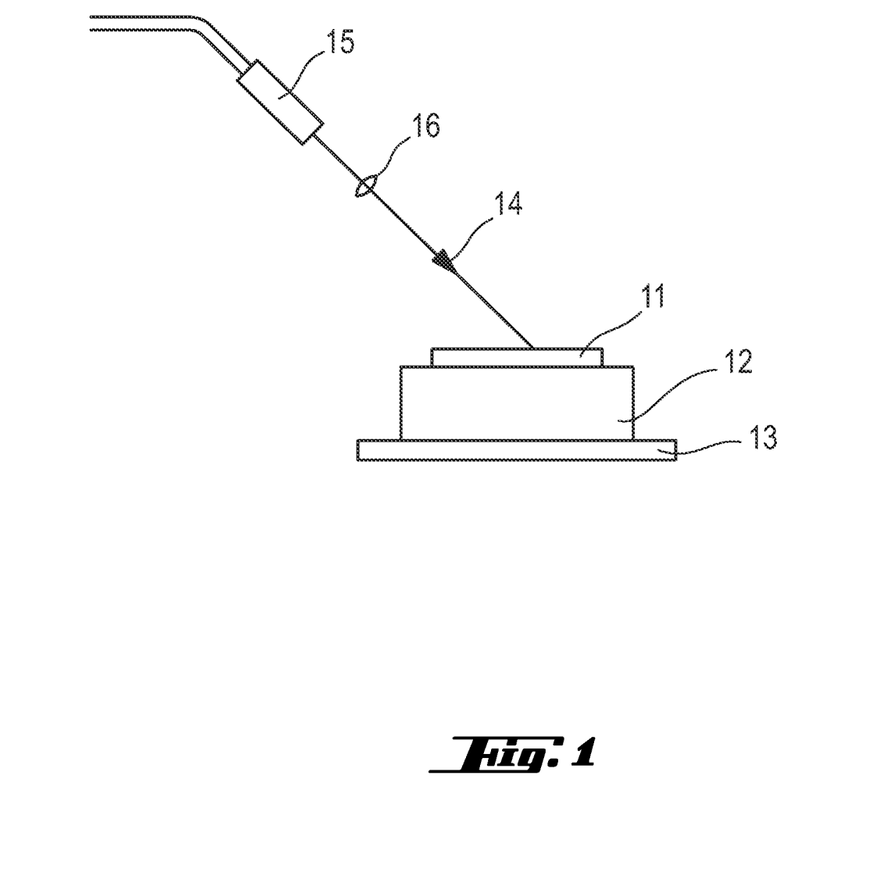
FIG. 1 is a schematic diagram of a laser irradiation process of a basic body as described in Example 1.
Figure 2:
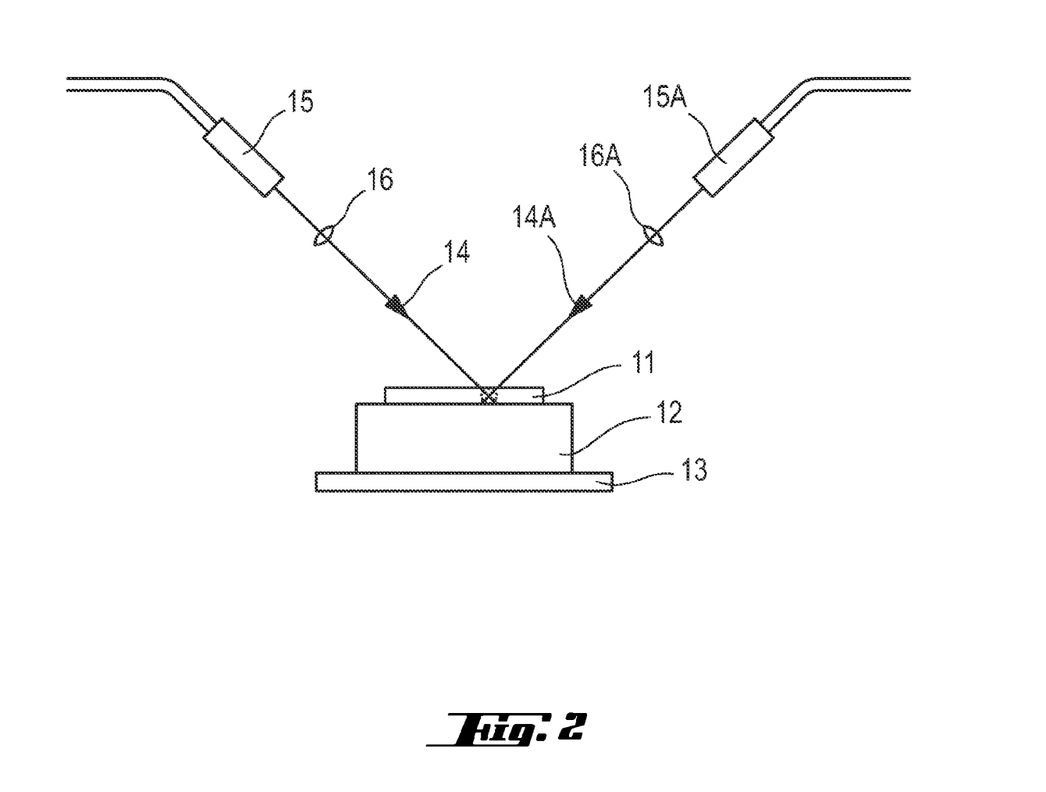
FIG. 2 is a schematic diagram of a laser irradiation process utilizing two beams that are collimated to increase the effective energy absorbed by the basic body.
Figure 3:
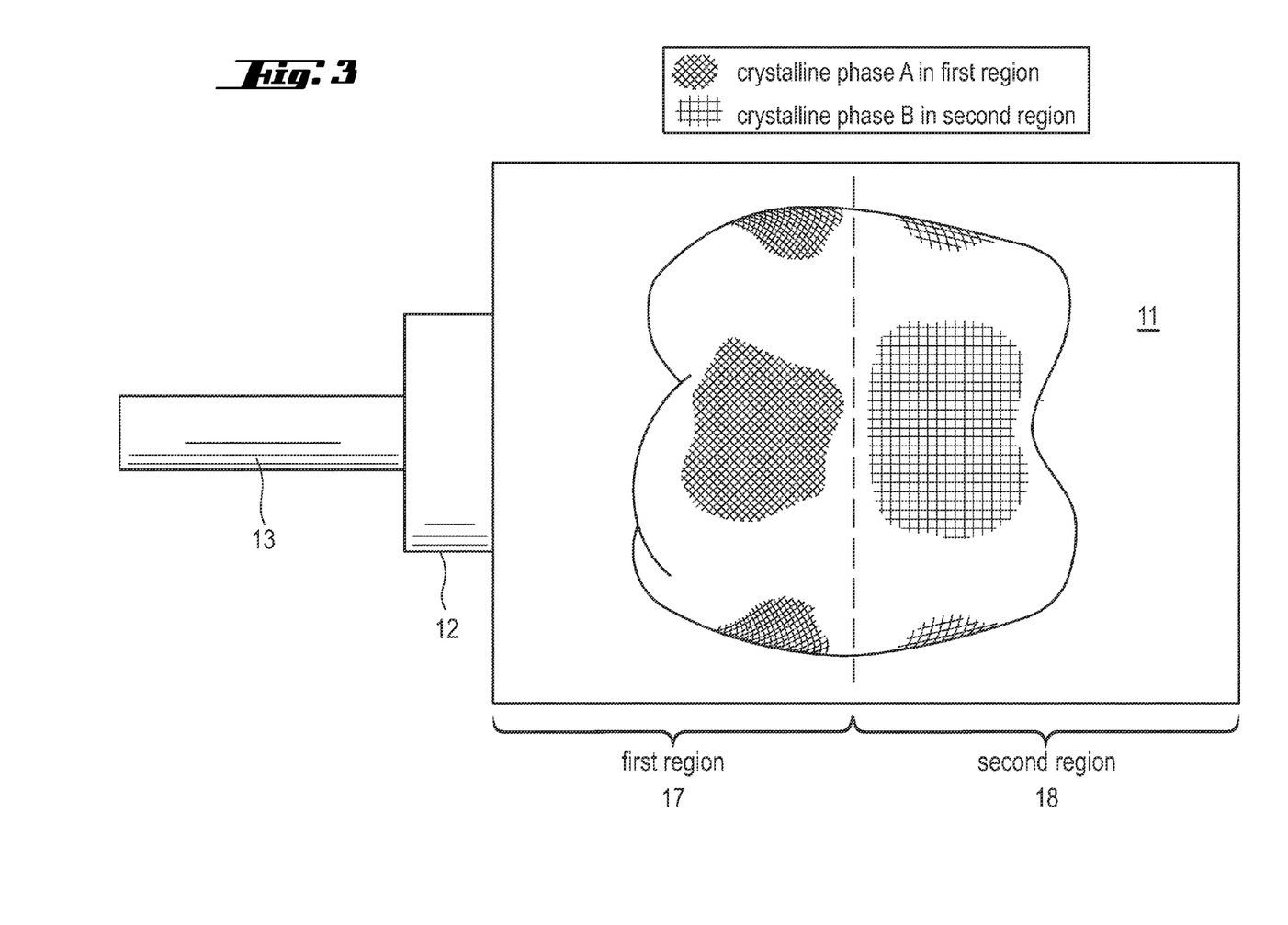
FIG. 3 is a top plan view of a basic body subjected to a first conversion step to induce formation of a crystalline phase A in a first region and a second conversion step to induce formation of a crystalline phase B in a second region, and showing an outline of the shape a prosthetic element for a dental restoration to be cut from the basic body.
Figure 4:
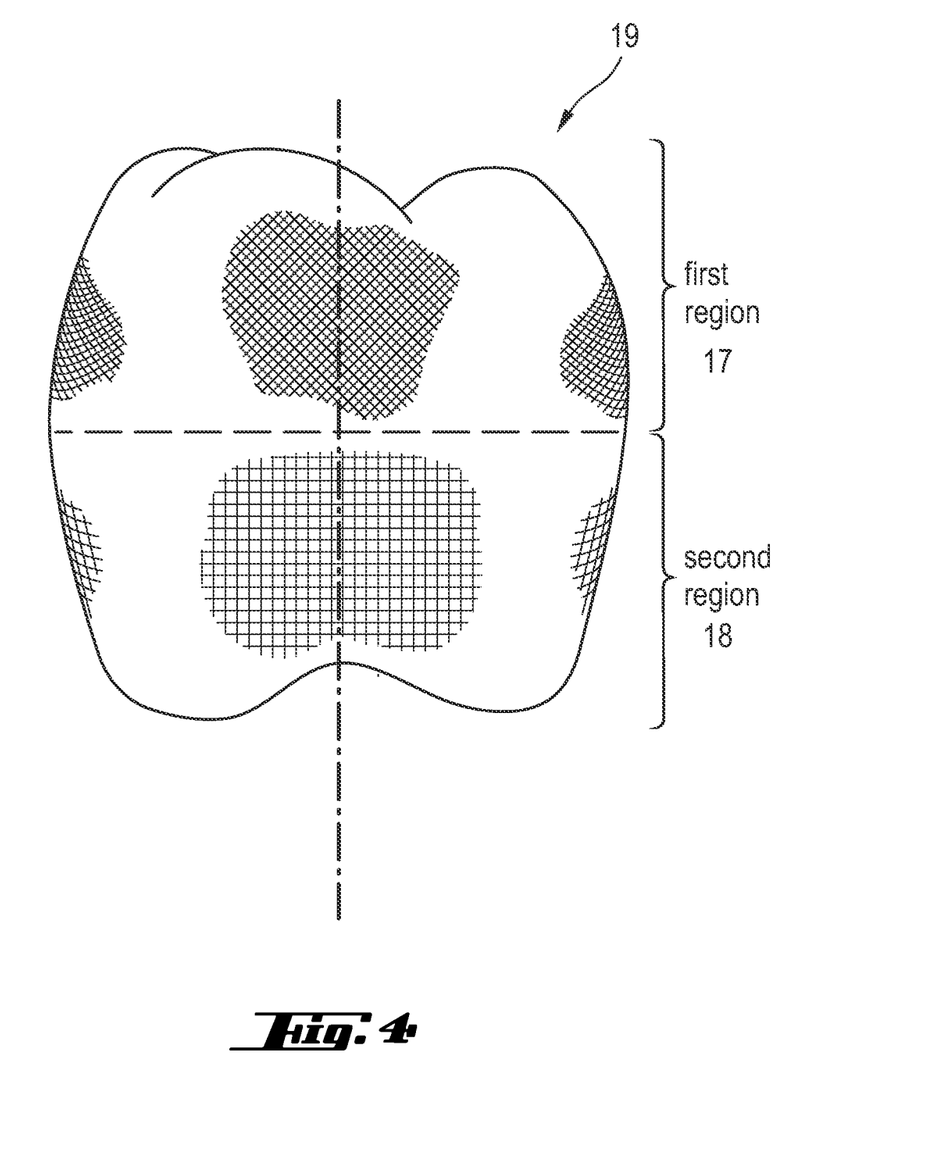
FIG. 4 is a schematic view of a prosthetic element cut from the basic body of FIG. 3, including first and second regions.
Figure 5:
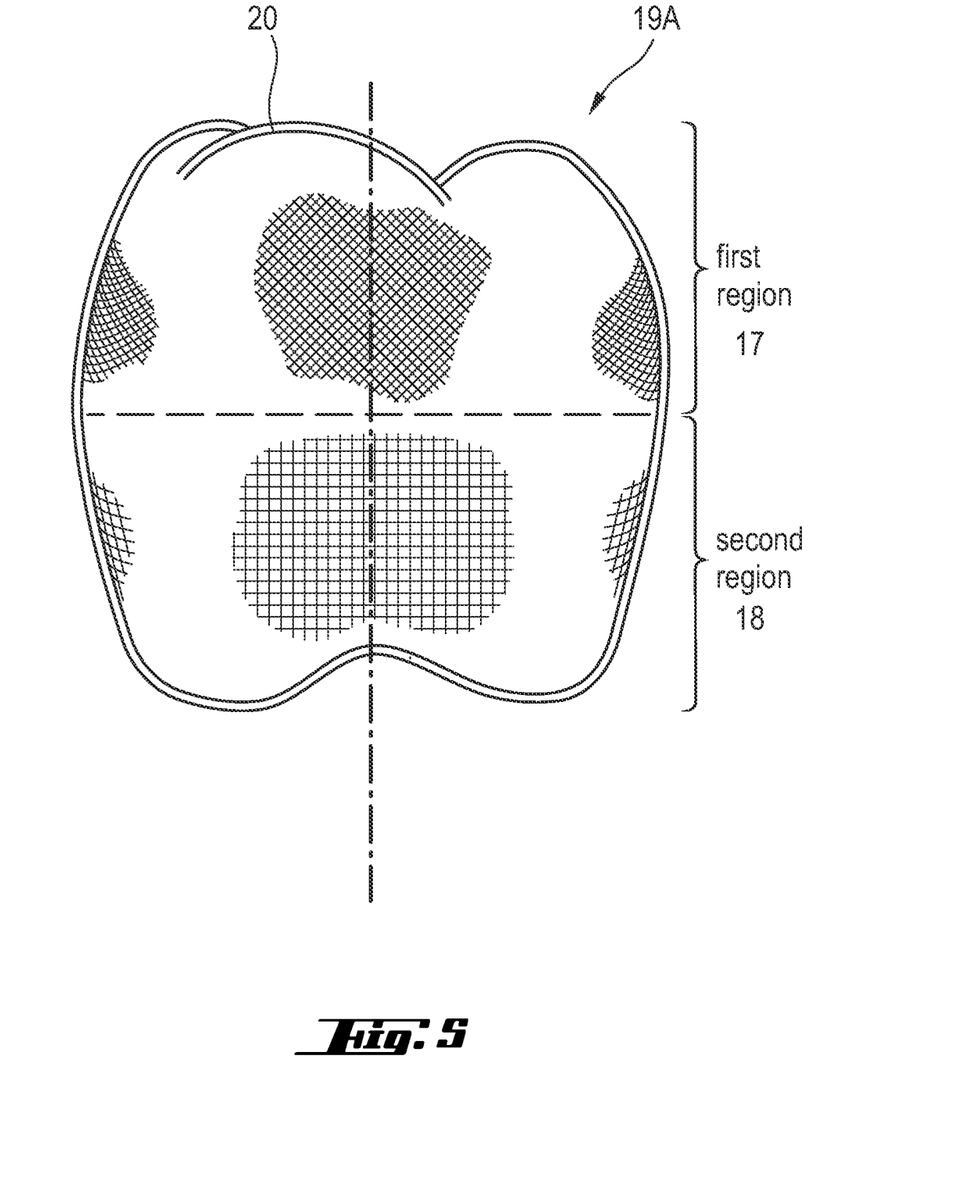
FIG. 5 is a schematic view of a final prosthetic element similar to FIG. 4 but including a melted outer surface.

A bar shaped sample 11 having the above composition is put on a ceramic base plate 12 (table) which itself is arranged on a metal support 13. This arrangement is placed in a chamber where the sample is treated by laser irradiation 14 using a LIMO high power continuous wave (cw) diode laser 15 (wavelength $\lambda$=808 nm, optical power=max. 350 W, spot diameter $d_F$=6 mm, uniform beam profile). The laser beam is thereby directed through a focusing lens 16.

More specific details regarding the laser irradiation in Experiments No.s 1.1 and 1.2 are given in the following:

| Experiment No. | # | 1.1 | 1.2 |
|---|---|---|---|
| Sample Position | | on table | on table |
| Sample State | | not nucleated | not nucleated |
| Beam Propagation | | focused angle 45° | focused angle 45° |
| Beam Diameter | mm | 6 | 6 |
| Optical Power | W | 180 | 180 |
| Intensity | W/cm² | 636.6 | 636.6 |
| Irradiation time | Min | 5 | 7 |

A comparison of Experiments 1.1 and 1.2 reveals that during the laser irradiation treatment a translucent violet colour starts to spread from the top to the bottom, followed by a white colour propagating from the centre of the sample, leaving a white crystalline phase in the centre with blue violet surroundings.

Example 2

Samples having the above composition are preheated in a first step during 1 min at 150 W and 1 min at 120 W before laser irradiation treatment using the laser specified in Example 1. More specific details regarding the laser irradiation in Experiment No. 2 are given in the following:

| Experiment No. | # | 2 |
|---|---|---|
| Sample Position | | on table |
| Sample State | | nucleated glass |
| Beam Propagation | | focused angle 45° |
| Beam Diameter | mm | 6 |
| Optical Power | W | 190 |
| Intensity | W/cm$^2$ | 672.0 |
| Irradiation time | Min | 3 |

By this treatment, a glass-ceramic sample comprising crystalline phases of white and yellow colour is obtained. The presence of the crystalline phases generated by laser irradiation is confirmed by XRD (X-ray diffraction) measurements which reveal the presence of 39.8% of beta-spodumene (LiAlSi$_2$O$_6$), 16.3% of lithium disilicate, 0.8% of dilithium phyllo-disilicate, 6.1% of lithiophosphate (Li$_3$PO$_4$), and 0.4% of petalite (LiAlSi$_4$O$_{10}$).

Thus, the examples confirm crystallization in the samples by laser irradiation energy using a laser having a wavelength of 808 nm.

(Comparative) Example 3

For comparative reasons, a sample having the composition defined above for Examples 1 and 2 is treated by laser irradiation using a picosecond laser (wavelength λ=355 nm (UV)) with a pulse duration of less than 12 picoseconds (ultra-short pulse).

By the process of Example 3, no crystallized areas inside the sample are obtained. Rather, ablation at the surface of the sample is detected.

(Comparative) Example 4

In a further comparative example, a sample having the composition defined above for Examples 1, 2 and 3 is treated by laser irradiation using a nanosecond laser (wavelength λ=355 nm (UV)) with a pulse duration of less than 20 nanoseconds.

Several laser intensities, focal positions and laser beam diameters are tested. At low laser intensities, no crystallization is detected. Higher laser intensities engenders thermal stresses that result in cracks along with a melting and ablation on the sample surface.

The invention claimed is:

1. A process for preparing a prosthetic element comprising a glass-ceramic body, said process comprising
   a) providing a basic body comprising an amorphous glass phase and containing the components of the glass-ceramic body to be prepared, and
   b) transferring energy to the basic body to induce conversion of a starting material of the basic body into at least one crystalline phase in a confined region, wherein
   energy is transferred to the confined region of the basic body by laser irradiating said region with a laser beam having a wavelength of at least 500 nm; and
   a first region of the basic body is subjected to a first conversion step to induce formation of a crystalline phase A in the first region, and a second region of the basic body different from the first region is subjected to a second conversion step to induce formation of a crystalline phase B in the second region, wherein the crystalline phase A formed in the first region is different from the crystalline phase B formed in the second region.

2. The process according to claim 1, wherein the laser beam has a wavelength of at least 600 nm.

3. The process according to claim 1, wherein the basic body is heated in the region through laser irradiation.

4. The process according to claim 1, wherein laser irradiation is performed using at least one continuous wave laser.

5. The process according to claim 1, wherein laser irradiation is performed by superposed application of two or more laser beams.

6. The process according to claim 1, wherein the starting phase is amorphous.

7. The process according to claim 1, wherein the basic body is made of an amorphous glass material.

8. The process according to claim 1, further comprising heating the basic body.

9. The process according to claim 8, wherein the basic body is heated to a first temperature before laser irradiation.

10. The process according to claim 9, wherein the first temperature lies in a range of from about 300° C. to about 750° C.

11. The process according to claim 9, wherein the first temperature lies in a range of from about 400° C. to about 750° C.

12. The process according to claim 9, wherein the first temperature lies in a range of from about 600° C. to about 750° C.

13. The process according to claim 9, wherein the first temperature is about 660° C.

14. The process according to claim 1, wherein the glass-ceramic body comprises 65 to 72 wt-% SiO$_2$, at least 8 wt-% of Li$_2$O, and at least 8 wt-% of Al$_2$O$_3$ based on a total weight of the composition.

15. The process according to claim 1, wherein the glass-ceramic body comprises at least one absorption-increasing ion selected from the group consisting of Nd$^{3+}$, Fe$^{2+}$, Fe$^{3+}$, V$^{2+}$, V$^{3+}$, V$^{4+}$, V$^{5+}$, Co$^{2+}$, Cr$^{4+}$, Cr$^{6+}$ and Mn$^{2+}$, and mixtures thereof.

16. The process according to claim 1, wherein the proportion of the crystalline phase A is higher in the first region than in the second region and the proportion of the crystalline phase B is higher in the second region than in the first region.

17. The process according to claim 1, wherein the at least one crystalline phase comprises at least one component selected from the group consisting of lithium metasilicate (Li$_2$SiO$_3$), lithium disilicate (Li$_2$Si$_2$O$_5$), lithium aluminosilicate (LiAlSi$_2$O$_6$, LiAlSiO$_4$, LiAlSi$_3$O$_8$ and/or LiAlSi$_4$O$_{10}$), and Li$_3$PO$_4$.

18. The process according to claim 1, wherein the crystalline phase A comprises lithium disilicate as main crystalline phase, and the crystalline phase B comprises lithium aluminosilicate as main crystalline phase.

19. The process according to claim 1, wherein the proportion of the crystalline phase A in the first region changes to the crystalline phase B in the second region in a gradual manner.

20. The process according to claim 1, wherein
the prosthetic element is a dental prosthetic element comprising a glass-ceramic body with an enamel area and a dentin area corresponding to the respective areas of a natural tooth, and
the first region comprising the crystalline phase A is formed in the enamel area, and the second region comprising the crystalline phase B is formed in the dentin area.

21. The process according to claim 1, further comprising melting an outermost surface of the basic body or the glass-ceramic body by means of laser irradiation followed by solidification of the melted material, thereby providing a gloss to the prosthetic element.

22. The process according to claim 1, further comprising cutting the basic body or the glass-ceramic body into the desired shape for the final prosthetic element, the cutting being performed by means of laser irradiation.

23. The process according to claim 1, wherein the laser beam has a wavelength of at least 700 nm.

24. The process according to claim 1, wherein the laser beam has a wavelength of at least 800 nm.

25. The process according to claim 1, wherein laser irradiation is performed using at least one continuous wave high power diode laser.

* * * * *